United States Patent [19]

Ishikawa et al.

[11] Patent Number: 5,258,535

[45] Date of Patent: Nov. 2, 1993

[54] METHOD FOR THE CHLORINATION OF A SILICON COMPOUND

[75] Inventors: Mitsuo Ishikawa; Kunai Atsutaka, both of Hiroshima; Yasushi Yamamoto, Gunma, all of Japan

[73] Assignee: Shin-Etsu Chemical Co., Ltd., Tokyo, Japan

[21] Appl. No.: 23,444

[22] Filed: Feb. 26, 1993

[30] Foreign Application Priority Data

Feb. 28, 1992 [JP] Japan .................. 4-078711

[51] Int. Cl.$^5$ .............................. C07F 7/08
[52] U.S. Cl. .................... 556/430; 556/477
[58] Field of Search ................ 556/430, 477

[56] References Cited

U.S. PATENT DOCUMENTS

| | | | |
|---|---|---|---|
| 3,231,333 | 1/1966 | Jenkner | 556/477 |
| 4,053,495 | 10/1977 | Deinhammer et al. | 556/477 |
| 4,665,209 | 5/1987 | Corriu et al. | 556/477 X |

FOREIGN PATENT DOCUMENTS 1668313  5/1971  Fed. Rep. of Germany .
2014427  4/1970  France .
978621  12/1964  United Kingdom .

OTHER PUBLICATIONS

Chemical Abstracts, vol. 102 (1985), Abstract No. 178275f, Belyaev, V. N. et al., p. 769.

*Primary Examiner*—Paul F. Shaver
*Attorney, Agent, or Firm*—Millen, White, Zelano & Branigan

[57] ABSTRACT

A novel method is proposed for the chlorination of a silicon compound having, in a molecule, at least one hydrogen atom directly bonded to the silicon atom. The method comprises the step of reacting the starting silicon compound with anhydrous copper (II) chloride as a chlorinating agent in the presence of copper (I) iodide as a catalyst so as to substitute a chlorine atom for the silicon-bonded hydrogen atom. When the starting silicon compound has two or more of silicon-bonded hydrogen atoms, the chlorination reaction proceeds stepwise so that the inventive method provides a possibility of selective chlorination.

6 Claims, No Drawings

METHOD FOR THE CHLORINATION OF A SILICON COMPOUND

BACKGROUND OF THE INVENTION

The present invention relates to a novel method for the chlorination of a silicon compound. More particularly, the invention relates to a method, starting from a silicon compound having at least one hydrogen atom directly bonded to the silicon atom, for the preparation of a chlorinated silicon compound by selectively replacing a part or all of the silicon-bonded hydrogen atoms in the starting silicon compound with chlorine atoms.

As is well known in the technology of silicone products, silicon compounds or silane compounds having, per molecule, at least one silicon-bonded hydrogen atom and at least one silicon-bonded chlorine atom, such as trichlorosilane, methyl dichlorosilane, dimethyl chlorosilane, methyl phenyl chlorosilane and the like, are very useful. These silane compounds or, in particular, methyl dichlorosilane, dimethyl chlorosilane and the like are industrially prepared by the so-called "direct method" reported by E. G. Rochow, et al. in U.S. Pat. No. 2,380,995 and Journal of the American Chemical Society, volume 67, page 1772 (1945). Alternatively, trichlorosilane, which is obtained by the reaction of elementary silicon and hydrogen chloride, can be used as an intermediate from which these silane compounds can be derived.

When it is desired to introduce an ordinary organic group into the molecule of a silane compound in the preparation of these silane compounds, several methods are known in the prior art including:

(1) a method described in Organometallic Compounds of the Group IV Elements, by A. G. MacDiarmid, editor, volume 1, pages 106 to 536 (1968), in which the silicon-bonded chlorine atom in the silane compound is replaced with the organic group R by using an organometallic compounds, e.g., Grignard reagent, according to the reaction equation

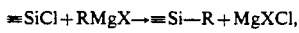

in which X is a halogen atom, and (2) a method reported by J. L. Speier, et al. in Journal of the American Chemical Society, volume 79, page 974 (1957) utilizing the so-called hydrosilation reaction between the silicon-bonded hydrogen atom in the silane compound and an α-olefin compound of the formula $CH_2=CH-R$ promoted by a platinum compound as a catalyst according to the reaction equation

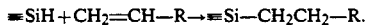

The above described first method utilizing an organometallic compound, which is applicable to the synthesis of a silane compound having a silicon-bonded hydrogen atom and a silicon-bonded chlorine atom in a molecule, is not suitable for use when such an organometallic compound cannot be used as in the case where the silane compound has a halogen-substituted organic group so that the only method applicable thereto is the above described second method. This method of hydrosilation, however, is not without problems in respects of the low reaction velocity when the silane compound has two or more silicon-bonded hydrogen atoms in a molecule and uncontrollability of the number of the organic groups introduced into a molecule of the silane compound.

Accordingly, the substitution reaction between a silicon-bonded hydrogen atom and a silicon-bonded chlorine atom provides a possibility for the synthesis in general, of which the reducing reaction of a silicon-bonded chlorine atom Si—Cl into a silicon-bonded hydrogen atom Si—H comes first. The reducing reaction can be performed in several different ways including a method of reduction in a polar solvent such as amides, imides and the like with sodium borohydride $NaBH_4$ or sodium hydride NaH as the reducing agent as disclosed in Japanese Patent Publication 55-34798, a method reported in Journal of Organometallic Chemistry, volume 18, page 371 (1969), in which dimethyl dichlorosilane is reacted with diethylamine to produce dimethyl (N,N-diethylamino) chlorosilane which is reduced with lithium aluminum hydride $LiAlH_4$ to give dimethyl (N,N-diethylamino) silane followed by the substitution of chlorine atoms for the diethylamino groups and a method disclosed in a Russian journal Zhurnal Obschchii Khimii, volume 40, page 812 (1970), in which dimethyl dichlorosilane is reduced with sodium hydride in the presence of aluminum chloride. These methods, however, are each disadvantageous because the reaction procedure is very complicated requiring special skillfulness to cause a difficulty in the control of the reaction along with the poor selectivity of the reaction.

A still alternative method known is the method of partial chlorination of a polyhydrosilane compound. A most conventional chlorinating agent for this purpose is chlorine for the conversion of a silicon-bonded hydrogen atom Si—H into a silicon-bonded chlorine atom Si—Cl as is disclosed in Japanese Patent Publication 3-10636 and Japanese Patent Kokai 2-67289, 2-145591 and 2-157286. This method, however, is not applicable for the purpose of partial chlorination because the reaction proceeds too violently.

Other known methods for the substitution of a chlorine atom for a silicon-bonded hydrogen atom include a method reported by J. Curtice, et al. in Journal of the American Chemical Society, volume 79, page 4754 (1957) and by Y. Nagai, et al. in Journal of Organometallic Chemistry, volume 9, page 21 (1967) according to which a chlorine-substitution reaction takes place between a hydrosilane compound and carbon tetrachloride in the presence of benzoyl peroxide as a catalyst and a method reported by Y. Nagai, et al. in Kogyo Kagaku Zasshi, volume 71, page 112 (1968) by using palladium chloride as a catalyst. These methods are also not suitable when partial hlorination is desired of a silicon compound having a plurality of silicon-bonded hydrogen atoms in a molecule.

SUMMARY OF THE INVENTION

The present invention accordingly has an object to provide a method for the preparation, starting from a silicon compound having at least one silicon-bonded hydrogen atom, of a silicon compound of which a part or all of the silicon-bonded hydrogen atoms are selectively replaced with chlorine atoms to a desired extent of chlorination.

Thus, the method of the invention for the chlorination of a silicon compound having at least one hydrogen atom directly bonded to the silicon atom comprises the step of reacting the silicon compound with anhydrous copper (II) chloride in the presence of copper (I) iodide.

The above defined inventive method is applicable to the chlorination of not only hydrosilane compounds but also hydropolysilane compounds such as 1,1,2,2-tetraethyl disilane, 1,1,2,2-tetraethyl chlorodisilane, 1,2-dimethyl-1,2-diphenyl disilane and 1,2-dimethyl-1,2-diphenyl chlorodisilane and hydropolysiloxanes such as 1,1,3,3-tetramethyl disiloxane.

DETAILED DESCRIPTION OF THE PREFERRED EMBODIMENTS

As is described above, the most characteristic feature of the inventive method consists in the use of a unique chlorinating agent which is anhydrous copper (II) chloride and a unique catalyst which is copper (I) iodide, by virtue of which the chlorination reaction can be controlled to proceed to a desired stage when the reaction conditions are adequately selected.

The chlorination reaction according to the inventive method proceeds step-wise in successive reactions according to the following reaction equations taking methyl phenyl silane as a typical starting silicon compound:

$$MePhSiH_2 + 2CuCl_2 \rightarrow MePhSiHCl + (2CuCl) \cdot HCl;$$

and $$MePhSiHCl + 2CuCl_2 \rightarrow MePhSiCl_2 + (2CuCl) \cdot HCl,$$

in which Me is a methyl group and Ph is a phenyl group.

The classes of the silicon compounds to which the inventive method is applicable include hydrosilane compounds represented by the general formula $$R^1{}_a SiH_b Cl_{4-a-b},$$

in which $R^1$ is an unsaturated or saturated monovalent hydrocarbon group having 1 to 20 carbon atoms, which optionally is substituted, the subscript a is 0 or a positive integer not exceeding 3 and the subscript b is a positive integer not exceeding 4 with the proviso that a+b does not exceed 4, hydropolysilane compounds represented by the general formula $$R^2-(-SiR^2{}_2-)_n-SiR^2{}_3,$$

in which $R^2$ is a hydrogen atom, a chlorine atom or an unsaturated or saturated monovalent hydrocarbon group having 1 to 20 carbon atoms, which optionally is substituted, at least one of the groups denoted by $R^2$ in a molecule being a hydrogen atom, and the subscript n is a positive integer not exceeding 5, and hydropolysiloxane compounds represented by the general formula, $$R^3-(-SiR^3{}_2-O-)_m-SiR^3{}_3,$$

in which $R^3$ is a hydrogen atom, a chlorine atom or an unsaturated or saturated monovalent hydrocarbon group having 1 to 20 carbon atoms, which optionally is substituted, at least one of the groups denoted by $R^3$ in a molecule being a hydrogen atom, and the subscript m is a positive integer not exceeding 5.

The monovalent hydrocarbon group denoted by $R^1$, $R^2$ or $R^3$ in the above given general formulas is exemplified by alkyl groups such as methyl, ethyl, n-propyl, isopropyl, n-butyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups, cycloalkyl groups such as cyclopentyl, cyclohexyl, cycloheptyl, cyclononyl, cy-cloundecyl, cyclododecyl, cyclotridecyl, cyclotetradecyl, cyclopentadecyl, cyclohexadecyl, cycloheptadecyl, cyclooctadecyl, cyclononadecyl and cycloeicosyl groups, alkenyl groups such as vinyl, allyl, 3-butenyl, 4-pentenyl and 5-hexenyl groups, cycloalkenyl groups such as 3-cyclopentenyl, 1-cyclohexenyl, 2-cyclohexenyl, 1-cyclododecenyl and 6-cyclododecenyl groups, aryl groups such as phenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,6-trimethylphenyl, 2-ethylphenyl, 3-ethylphenyl, 4-ethylphenyl, 3-propylphenyl, 4-butylphenyl, 1-naphthyl and 2-naphthyl groups, aralkyl groups such as benzyl, 2-phenylethyl, 3-phenylpropyl and 4-phenylbutyl groups, halogen-substituted hydrocarbon groups such as 3-chloropropyl, 3-bromopropyl, perfluoroalkyl-substituted ethyl groups of the general formula $RfCH_2CH_2-$, in which Rf is a perfluoroalkyl group of the formula $C_xF_{2x+1}-$, x being 1, 3, 4, 6 or 8, groups of the general formula $F(CXFCF_2O)_pCXF-$, in which X is a fluorine atom or a trifluoromethyl group and p is a positive integer not exceeding 5, 3-chlorophenyl, 4-chlorophenyl, 3-bromophenyl and 3,4-dichlorophenyl groups, groups having an ether linkage in a molecule such as 3-methoxypropyl, 3-phenoxypropyl, 3-methoxyphenyl, 4-methoxyphenyl, 3-ethoxyphenyl and 4-ethoxyphenyl groups, and so on. The examples of the groups above are given merely as typical ones and should not be construed to be limitative of the applicability of the inventive method which is applicable to any silicon compounds provided that the compound is stable under the reaction conditions.

Besides the above named substituted or unsubstituted hydrocarbon groups, the groups denoted by $R^2$ and $R^3$ in the general formulas representing hydropolysilanes and hydropolysiloxanes, respectively, each can be a hydrogen atom or a chlorine atom and at least one of the groups denoted by $R^2$ and at least one of the groups denoted by $R^3$ in a molecule of the hydropolysilane or hydropolysiloxane, respectively, must be a hydrogen atom directly bonded to a silicon atom.

As is understood from the reaction equations given before for methyl phenyl silane $MePhSiH_2$ as an example, 2 moles of anhydrous copper (II) chloride as the chlorinating agent are stoichiometrically required for the conversion of one mole of the silicon-bonded hydrogen atoms into silicon-bonded chlorine atoms. Since the process according to the inventive method proceeds stepwise in successive reactions, the amount of anhydrous copper (II) chloride to be used depends on the number of the silicon-bonded hydrogen atoms to be converted into silicon-bonded chlorine atoms. As a rough measure, from 1.8 to 2.2 moles of anhydrous copper (II) chloride should be used when mole of the silicon-bonded hydrogen atoms are desired to be converted into silicon-bonded chlorine atoms.

In conducting chlorination of a hydrosilane compound according to the inventive method, it is optional that the reaction mixture is diluted by the addition of a suitable organic solvent. Examples of preferable organic solvents include diethyl ether and tetrahydrofuran as well as mixtures thereof. The amount of the organic solvent, when used, is in the range, for example, from 500 ml to 5000 ml per mole of the anhydrous copper (II) chloride though not particularly limitative provided that the reaction mixture has such a consistency as to ensure smooth agitation of the mixture and efficient contacting between the reactants.

The reaction temperature is preferably in the range from 0° C. to 30° C. though not particularly limitative provided that the reaction proceeds smoothly to convert the silicon-bonded hydrogen atoms in the starting silicon compound into silicon-bonded chlorine atoms and no substantial side reactions take place due to the copper (II) chloride, copper (I) iodide or the intermediate copper (I) chloride hydrochloride (2 CuCl)·HCl.

The chlorination reaction according to the inventive method is promoted by copper (I) iodide although the mechanism of the reaction is not well understood. A presumable mechanism is that the first step of the reaction is the reaction of copper (I) iodide with the silicon-bonded hydrogen atom to form a silicon-bonded iodine atom Si—I which is converted into a silicon-bonded chlorine atom Si—Cl by the reaction with copper (II) chloride with regeneration of copper (I) iodide. Accordingly, the amount of copper (I) iodide to be added to the reaction mixture can be a so-called catalytic amount which means an amount capable of smoothly promoting the reaction by the catalytic activity thereof. As a rough measure, the amount of copper (I) iodide is in the range from 0.1 to 5% by weight or, preferably, from 0.5 to 2% by weight based on the amount of the copper (II) chloride.

The above given description relative to the chlorinating agent, catalyst, solvent and reaction temperature is applicable irrespective of the types of the starting silicon compound which may be a hydrosilane compound, hydropolysilane compound or hydropolysiloxane compound. The molecular structure of the hydropolysilanes and hydropolysiloxanes is not limited to a straightly linear one but can be branched or cyclic. There is noted a possibility that the reactivity of a silicon-bonded hydrogen atom by the inventive chlorinating method is lower when the silicon-bonded hydrogen atom is in a pendant group on the main chain than when it is at the molecular chain end. If this difference in the reactivity be actually held, the inventive method provides a possibility of selective chlorination of the silicon-bonded hydrogen atoms at the molecular chain ends.

In the following, the method of the present invention is described in more detail by way of examples.

EXAMPLE 1

Into a four-necked flask of 500 ml capacity equipped with a stirrer, reflux condenser and thermometer were introduced 15.3 g (0.125 mole) of methyl phenyl silane, 33.8 g (0.252 mole) of anhydrous copper (II) chloride, 1.23 g (0.00646 mole) of anhydrous copper (I) iodide and 300 ml of ether to form a reaction mixture which was agitated at room temperature for 36 hours. The precipitates of copper salts formed in the reaction mixture were removed by filtration and the filtrate, from which the solvent was removed by distillation, was subjected to distillation under reduced pressure to give 15.1 g of a fraction boiling at 76° to 78° C. under a pressure of 25 mmHg. The analytical results obtained for this liquid product shown below supported that the product was methyl phenyl chlorosilane of the formula $(CH_3)(C_6H_5)SiHCl$. The above mentioned yield of the product corresponds to 77% of the theoretical value.

|  | C, % | H, % |
|---|---|---|
| Elementary analysis |  |  |
| Calculated for $C_7H_9SiCl$ | 53.66 | 5.79 |
| Found | 53.62 | 5.96 |
| Mass-spectrometric analysis (m/e) | $M^+$: 156 | |
| Nuclear magnetic resonance absorption spectrometry | | |
| $^1$H-NMR($\delta$: solvent $CDCl_3$) | | |
| 0.80(d, J=3, 3Hz, $CH_3Si$) | | |
| 5.37(q, J=3, 3Hz, 1H, HSi) | | |
| 7.40–7.71(m, 5H, benzene ring) | | |
| $^{13}$C-NMR($\delta$: solvent $CDCl_3$) | | |
| 0.11($CH_3Si$) | | |
| 128.23, 130.87, 133.37, 133.62(C in benzene ring) | | |

EXAMPLE 2

The experimental procedure was similar to that in Example 1 by conducting the reaction in a reaction mixture consisting of 409.8 g (0.837 mole) of 2-(perfluorooctyl)ethyl methyl silane of the formula $(C_8F_{17}CH_2CH_2)(CH_3)SiH_2$ with twice by moles of anhydrous copper (II) chloride in tetrahydrofuran in the presence of anhydrous copper (I) iodide for 4 hours and 20 minutes. The product could be identified as 2-(perfluorooctyl)ethyl methyl chlorosilane of the formula $(C_8F_{17}CH_2CH_2)(CH_3)SiHCl$. The yield of this product corresponds to 72% of the theoretical value.

EXAMPLES 3 to 10

The reaction procedure in each of these examples was substantially the same as in Example 1 excepting replacement of the starting hydrosilane compound with those listed in the table below. The solvent used was ether in Examples 3 to 8, a 6:1 by volume mixture of ether and tetrahydrofuran in Example 9 and tetrahydrofuran in Example 10. The amount of the anhydrous copper (II) chloride was equimolar to the starting silane compound in all of the Examples excepting Example 8 in which the molar amount of the copper (II) chloride was twice of the starting silane compound. Table 1 below summarizes the formulas of the starting and product silane compounds, reaction time and yield of the product relative to the theoretical amount.

TABLE 1

| Example No. | Starting silane | Product silane | Reaction time, hours | Yield, % |
|---|---|---|---|---|
| 3 | $(CH_3)_2(C_6H_5)SiH$ | $(CH_3)_2(C_6H_5)SiCl$ | 13 | 82 |
| 4 | $(CH_3)(C_6H_5)_2SiH$ | $(CH_3)(C_6H_5)_2SiCl$ | 21 | 77 |
| 5 | $(C_4H_9)_2(CH_3)SiH$ | $(C_4H_9)_2(CH_3)SiCl$ | 70 | 87 |
| 6 | $(C_2H_5)_2SiH_2$ | $(C_2H_5)_2SiHCl$ | 43 | 68 |
| 7 | $(C_6H_5)SiH_3$ | $(C_6H_5)SiH_2Cl$ | 72 | 70 |
| 8 | $(C_6H_5)SiH_3$ | $(C_6H_5)SiHCl_2$ | 94 | 66 |
| 9 | $(CF_3C_2H_4)(CH_3)SiH_2$ | $(CF_3C_2H_4)(CH_3)SiHCl$ | 50 | 75 |
| 10 | $(CH_3)_2(tert\text{-}C_4H_9)SiH$ | $(CH_3)_2(tert\text{-}C_4H_9)SiCl$ | 70 | 75 |

EXAMPLE 11

The chlorination reaction was conducted in substantially the same manner as in Example 1 in a reaction mixture consisting of 10.0 g (0.0527 mole) of 1,1,2,2-tetraethyldisilane, 16.0 g (0.119 mole) of anhydrous copper (II) chloride, 0.304 g of anhydrous copper (I) iodide and 200 ml of ether. After 18 hours of the reaction time followed by isolation of the product, 6.8 g of 1,1,2,2-tetraethyl-1-chlorodisilane were obtained as a fraction boiling at 88° C. under a pressure of 20 mmHg. The yield of the product corresponds to 57% of the theoretical value. The analytical results of this product were as shown below.

|  | C, % | H, % |
|---|---|---|
| Elementary analysis |  |  |
| Calculated for $C_8H_{21}Si_2Cl$ | 46.00 | 10.13 |
| Found | 45.86 | 10.08 |
| Mass-spectrometric analysis (m/e) | $M^+$: 208 |  |
| Nuclear magnetic resonance absorption spectrometry |  |  |
| $^1$H-NMR($\delta$: solvent $CDCl_3$) |  |  |
| 0.70–1.10(m, 20H, $CH_3CH_2Si$) |  |  |
| 3.65(m, 1H, HSi) |  |  |
| $^{13}$C-NMR($\delta$: solvent $CDCl_3$) |  |  |
| 1.49, 7.01, 9.62, 9.67($CH_3CH_2Si$) |  |  |

In addition to the above product, 2.2 g of 1,1,2,2-tetraethyl-1,2-dichlorodisilane were obtained corresponding to a yield of 16% relative to the theoretical yield. The analytical results of this second product were as shown below.

| Mass-spectrometric analysis (m/e) | $M^+$: 242 |
|---|---|
| Nuclear magnetic resonance absorption spectrometry |  |
| $^1$H-NMR($\delta$: solvent $CDCl_3$) |  |
| 0.97–1.16(m, 20H, $CH_3CH_2Si$) |  |
| $^{13}$C-NMR($\delta$: solvent $CDCl_3$) |  |
| 6.81($CH_3$) |  |
| 8.54(—$CH_2$—) |  |

EXAMPLES 12 to 14

The experimental procedure in each of these Examples was substantially the same as in Example 1 excepting replacement of the starting hydrosilane compound with 1,1,2,2-tetraethyldisilane in Example 12 and 1,2-dimethyl-1,2-diphenyldisilane in Examples 13 and 14 and use of 4 moles, 2 moles and 4 moles of anhydrous copper (II) chloride in Examples 12, 13 and 14, respectively, per mole of the starting hydrodisilane compound. Table 2 below summarizes the formulas of the starting and product disilane compounds, reaction time and yield of the product relative to the theoretical amount. The symbols Me, Et and Ph denote a methyl, ethyl and phenyl group, respectively.

TABLE 2

| Example No. | Starting disilane | Product disilane | Reaction time, hours | Yield, % |
|---|---|---|---|---|
| 12 | $HEt_2Si$—$SiEt_2H$ | $ClEt_2Si$—$SiEt_2Cl$ | 8 | 92 |
| 13 | HMePhSi—SiMePhH | ClMePhSi—SiMePhH | 72 | 59 |
| 14 | HMePhSi—SiMePhH | ClMePhSi—SiMePhCl | 132 | 79 |

EXAMPLE 15

The chlorination reaction was conducted in substantially the same manner as in Example 1 in a reaction mixture consisting of 24.8 g (0.213 mole) of dimethyl tert-butyl silane, 58.0 g (0.432 mole) of anhydrous copper (II) chloride, 2.14 g (0.0112 mole) of anhydrous copper (I) iodide, 350 ml of ether and 150 ml of tetrahydrofuran. After 60 hours of the reaction time followed by isolation of the product, 23.6 g of dimethyl tert-butyl chlorosilane were obtained. This yield of the product corresponds to 73% of the theoretical value.

EXAMPLE 16

The chlorination reaction was conducted in substantially the same manner as in Example 1 in a reaction mixture consisting of 26.9 g (0.200 mole) of 1,1,3,3-tetramethyldisiloxane, 53.8 g (0.400 mole) of anhydrous copper (II) chloride, 1.9 g (0.010 mole) of anhydrous copper (I) iodide and 300 ml of ether. After 25 hours of the reaction time followed by isolation of the product, 16.9 g of 1,1,3,3-tetramethyl-1-chlorodisiloxane and 10.2 g of 1,1,3,3-tetramethyl-1,3-dichlorodisiloxane were obtained. The yields of these disiloxane products correspond to 50% and 26%, respectively, of the theoretical values.

What is claimed is:

1. A method for the chlorination of a silicon compound having at least one hydrogen atom directly bonded to the silicon atom per molecule, which comprises the step of reacting the silicon compound with anhydrous copper (II) chloride in the presence of copper (I) iodide.

2. A method according to claim 1 for the chlorination of a hydrosilane compound represented by the general formula $R^1_a SiH_b Cl_{4-a-b}$, in which $R_1$ is an unsubstituted or substituted monovalent hydrocarbon group having 1 to 20 carbon atoms, the subscript a is 0, 1, 2 or 3 and the subscript b is 1, 2, 3 or 4 with the proviso that a+b is a positive integer not exceeding 4, which comprises the step of reacting the hydrosilane compound with anhydrous copper (II) chloride in the presence of copper (I) iodide.

3. A method according to claim 1 for the chlorination of a hydropolysilane compound represented by the general formula $R^2(SiR^2_2)_n SiR^2_3$, in which $R^2$ is, each independently from the others, a hydrogen atom, chlorine atom or unsubstituted or substituted monovalent hydrocarbon group having 1 to 20 carbon atoms, at least one of the groups denoted by $R^2$ being a hydrogen atom, the subscript n is a positive integer not exceeding 5, which comprises the step of reacting the hydropolysilane compound with anhydrous copper (II) chloride in the presence of copper (I) iodide.

4. A method for the chlorination of a hydropolysiloxane compound represented by the general formula $R^3(SiR^3_2O)_m SiR^3_3$, in which $R^3$ is, each independently from the others, a hydrogen atom, chlorine atom or unsubstituted or substituted monovalent hydrocarbon group having 1 to 20 carbon atoms, at least one of the groups denoted by $R^3$ being a hydrogen atom, the subscript m is a positive integer not exceeding 5, which comprises the step of reacting the hydropolysiloxane compound with anhydrous copper (II) chloride in the presence of copper (I) iodide.

5. A method according to claim 1 for the chlorination of a hydrodisilane compound selected from the group consisting of 1,1,2,2-tetraethyl disilane, 1,1,2,2-tetraethyl chloorodisilane, 1,2-dimethyl-1,2-diphenyl disilane and 1,2-dimethyl-1,2-diphenyl chlorodisilane which comprises the step of reacting the hydrodisilane compound with anhydrous copper (II) chloride in the presence of copper (I) iodide.

6. A method according to claim 1 for the chlorination of 1,1,3,3-tetramethyl disiloxane, which comprises the step of reacting the 1,1,3,3-tetramethyl disiloxane with anhydrous copper (II) chloride in the presence of copper (I) iodide.

* * * * *

UNITED STATES PATENT AND TRADEMARK OFFICE
CERTIFICATE OF CORRECTION

PATENT NO. : 5,258,535

DATED : November 2, 1993

INVENTOR(S) : Mitsuo ISHIKAWA et al.

It is certified that error appears in the above-identified patent and that said Letters Patent is hereby corrected as shown below:

Claim 2; Col. 8; Line 31:

Change $R_1$ to read -- $R^1$

Signed and Sealed this

Twenty-sixth Day of April, 1994

BRUCE LEHMAN

*Attest:*

*Attesting Officer*   *Commissioner of Patents and Trademarks*